(12) United States Patent
Shimotsu

(10) Patent No.: US 8,403,836 B2
(45) Date of Patent: Mar. 26, 2013

(54) LIGHT GUIDE, LIGHT SOURCE APPARATUS AND ENDOSCOPE SYSTEM

(75) Inventor: Shinichi Shimotsu, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 442 days.

(21) Appl. No.: 12/705,878

(22) Filed: Feb. 15, 2010

(65) Prior Publication Data

US 2010/0210911 A1    Aug. 19, 2010

(30) Foreign Application Priority Data

Feb. 13, 2009  (JP) ................... 2009-030805

(51) Int. Cl.
*A61B 1/06* (2006.01)
*G02B 6/36* (2006.01)

(52) U.S. Cl. .......... 600/182; 385/80; 385/126; 385/127; 385/128; 600/177

(58) Field of Classification Search ............. 600/182, 600/177; 385/80
See application file for complete search history.

(56) References Cited

U.S. PATENT DOCUMENTS

| | | | | |
|---|---|---|---|---|
| 4,199,238 A | * | 4/1980 | Boudreau | ............ 396/267 |
| 4,877,300 A | | 10/1989 | Newhouse et al. | |
| 5,800,349 A | * | 9/1998 | Isaacson et al. | ............ 600/323 |

(Continued)

FOREIGN PATENT DOCUMENTS

| JP | 2000-199864 A | 7/2000 |
|---|---|---|
| JP | 2003-086868 A | 3/2003 |
| JP | 2005-129863 A | 5/2005 |

OTHER PUBLICATIONS

The First Office Action, dated Jul. 23, 2012, issued in corresponding CN Application No. 201010171258.X, 9 pages in English and Chinese.

(Continued)

*Primary Examiner* — Clayton E Laballe
*Assistant Examiner* — Linda B Smith
(74) *Attorney, Agent, or Firm* — Sughrue Mion, PLLC

(57) ABSTRACT

A large diameter fiber is composed of a multimode optical fiber and provided with a fiber body having a constant diameter in an optical axis direction XA and a tapered section tapered in diameter toward a light exit surface. An adhesive member attaches the large diameter fiber inside a retaining hole of a tubular housing such that an outer circumferential surface of a tapered clad of the tapered section is entirely exposed to air to a predetermined depth from the light exit surface. A light passing space is a ring-like space formed between the exposed outer circumferential surface of the tapered clad and an inner circumferential surface of the tubular housing. Light in the tapered section is output from the light exit surface and partially leaked to the tapered clad. A part of the leaked light is released from the light passing space.

8 Claims, 4 Drawing Sheets

U.S. PATENT DOCUMENTS

| | | | |
|---|---|---|---|
| 5,852,692 A * | 12/1998 | Nightingale et al. | 385/43 |
| 5,888,194 A | 3/1999 | Utsumi et al. | |
| 6,282,342 B1 * | 8/2001 | Berkey et al. | 385/43 |
| 6,485,191 B1 * | 11/2002 | Sato | 385/73 |
| 6,746,160 B2 * | 6/2004 | Takeuti et al. | 385/84 |
| 7,083,334 B2 * | 8/2006 | Camporeale et al. | 385/80 |
| 7,922,654 B2 * | 4/2011 | Boutillette et al. | 600/160 |
| 2005/0207454 A1 * | 9/2005 | Starodoumov et al. | 372/4 |
| 2006/0030753 A1 | 2/2006 | Boutillette et al. | |
| 2006/0098934 A1 * | 5/2006 | Eyal et al. | 385/146 |
| 2008/0058629 A1 * | 3/2008 | Seibel et al. | 600/368 |
| 2009/0109698 A1 * | 4/2009 | Koyata et al. | 362/553 |
| 2011/0152619 A1 * | 6/2011 | Hixon | 600/135 |
| 2012/0065521 A1 * | 3/2012 | Richards-Kortum et al. | 600/476 |

OTHER PUBLICATIONS

Notification of Reasons for Refusal, dated Apr. 11, 2012, issued in corresponding JP Application No. 2009-030805, 4 pages in English and Japanese.

* cited by examiner

LIGHT GUIDE, LIGHT SOURCE APPARATUS AND ENDOSCOPE SYSTEM

FIELD OF THE INVENTION

The present invention relates to a light guide for transmitting light, and also to a light source apparatus and an endoscope system using this light guide.

BACKGROUND OF THE INVENTION

A large diameter optical fiber and a bundle fiber having a plurality of optical fibers bundled together are used as laser light guides for transmitting laser beams having specific wavelength(s), such as those for use in laser scalpels (see Japanese Patent Laid-Open Publication No. 2003-086868), and also used as light guides incorporated in endoscopes. The light guide of the endoscope transmits illumination light to illuminate a body cavity of a patient (see Japanese Patent Laid-Open Publication No. 2000-199864 and U.S. Pat. No. 5,888,194 corresponding to Japanese Patent Laid-Open Publication No. 9-166754). In addition, such optical fibers are used for data signal communications (see U.S. Pat. No. 4,877,300, corresponding to Japanese Patent Laid-Open Publication No. 2-163708).

The light guides described in Japanese Patent Laid-Open Publication No. 2000-199864 and U.S. Pat. No. 5,888,194 are required to illuminate as large an area as possible in the body cavity so as to facilitate finding a lesion. To illuminate a larger area, it is necessary to increase a divergence angle of exit light from the optical fiber.

As described in U.S. Pat. No. 4,877,300 and Japanese Patent Laid-Open Publication No. 2003-086868, tapering a light exit portion of the optical fiber enables to increase the divergence angle of the exit light. However, the use of the tapered optical fiber alone cannot increase the divergence angle enough to facilitate finding a lesion. It should be noted that, in U.S. Pat. No. 4,877,300, the tapered optical fiber is used for improving light coupling efficiency and conversion of a beam diameter. In Japanese Patent Laid-Open publication No. 2003-086868, the tapered optical fiber is used for increasing laser power density.

SUMMARY OF THE INVENTION

An object of the present invention is to provide a light guide, a light source apparatus and an endoscope system having a large illumination angle so as to illuminate a large area.

In order to achieve the above objects and other objects, a light guide of the present invention includes a tubular housing, a multimode optical fiber and a transparent adhesive member. The multimode optical fiber is inserted through the housing. The multimode optical fiber has a core and a clad covering an outer circumferential surface of the core. The core has a tapered core whose diameter decreases toward a light exit surface. The clad has a tapered clad whose outer circumferential surface is inclined to be tapered along an outer circumferential surface of the tapered core toward the light exit surface. The transparent adhesive member is provided between the housing and an outer circumferential surface of the clad. The adhesive member retains the multimode optical fiber in the housing. The adhesive member has a lower refractive index than the clad. The adhesive member has a light passing space hollowed out to a predetermined depth from the light exit surface so as to expose at least a part of the outer circumferential surface of the tapered clad to air.

It is preferable that the light passing space is a ring-like space formed between an inner surface of the housing and the outer circumferential surface of the tapered clad entirely exposed to air to the predetermined depth.

It is preferable that the light passing space is composed of a first space and a second space. Each of the first and second spaces has a tubular shape and is formed between the partly exposed outer circumferential surface of the tapered clad and the inner surface of the housing. It is preferable that the first space is provided in a location opposite to the second space relative to the tapered core and the tapered clad.

It is preferable that a radiation pattern of the light from the light exit surface is elliptical in shape.

It is preferable that a numerical aperture (NA) of the light from the light exit surface is at least 0.35.

It is preferable that the light passing space is formed by an attaching step and a removing step. In the attaching step, the multimode optical fiber is inserted into the housing and attached in the housing by providing the adhesive member containing a UV hardening adhesive and by hardening the adhesive member by UV irradiation. The adhesive member is provided between an outer circumferential surface of the clad and an inner surface of the housing in a state that the light exit surface of the multimode optical fiber and an end surface of the housing are made level with each other. In the removing step, laser in a UV wavelength range to be absorbed by the adhesive member is irradiated onto the adhesive member such that at least a part of the outer circumferential surface of the tapered clad is exposed to air to the predetermined depth from the light exit surface.

A light source apparatus includes a light source, a tubular housing, a multimode optical fiber, and a transparent adhesive member. The multimode optical fiber is inserted through the housing. The multimode optical fiber has a core and a clad covering an outer circumferential surface of the core. The core has a tapered core whose diameter decreases toward a light exit surface. The clad has a tapered clad whose outer circumferential surface is inclined to be tapered along an outer circumferential surface of the tapered core toward the light exit surface. The multimode optical fiber transmits light from the light source. The transparent adhesive member is provided between the housing and an outer circumferential surface of the clad. The adhesive member retains the multimode optical fiber in the housing. The adhesive member has a lower refractive index than the clad. The adhesive member has a light passing space hollowed out to a predetermined depth from the light exit surface so as to expose at least apart of the outer circumferential surface of the tapered clad to air.

An endoscope system includes the light source apparatus, an endoscope and an image processing apparatus. The endoscope has an image sensor. The image sensor takes an image of a body cavity illuminated with the light from the light exit surface. The image processing apparatus is connected to the endoscope. The processing apparatus processes a signal from the image sensor and forms an image.

According to the present invention, the divergence angle of the exit light from the optical fiber is large. As a result, the exit light illuminates a large area, which facilitates finding a lesion.

BRIEF DESCRIPTION OF THE DRAWINGS

The above and other objects and advantages of the present invention will be more apparent from the following detailed description of the preferred embodiments when read in connection with the accompanied drawings, wherein like reference numerals designate like or corresponding parts throughout the several views, and wherein.

DESCRIPTION OF THE PREFERRED EMBODIMENTS

Figure 1:
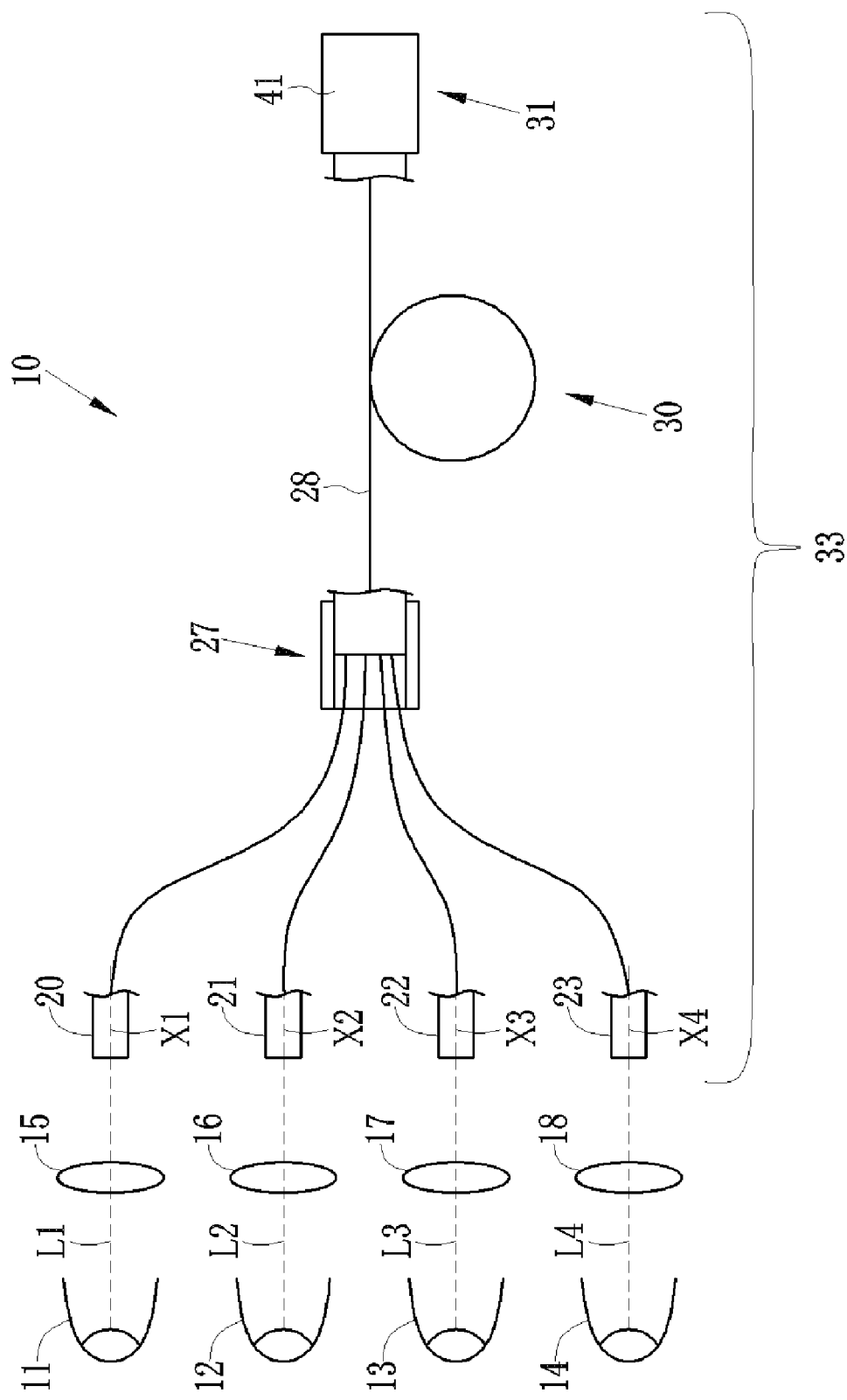
FIG. 1 is a schematic view of light source apparatus of the first embodiment of the present invention.

As shown in FIG. 1, a light source apparatus 10 of the first embodiment of the present invention has light sources 11 to 14, condenser lenses 15 to 18, small diameter optical fibers (hereinafter referred to as small diameter fibers) 20 to 23, a fiber connector 27, a large diameter optical fiber (hereinafter referred to as large diameter fiber) 28, a speckle reducer 30 and a light exit section 31 having an exit surface. In the light exit section 31, the large diameter fiber 28 is retained inside a tubular housing 41.

The small diameter fibers 20 to 23 are bundled with a ferrule or the like on the light output side. A light guide 33 is composed of two or more small diameter fibers, in this case, the small diameter fibers 20 to 23, and the large diameter fiber 28. Since the light guide is an optical fiber that transmits light, any one of the small diameter fibers 20 to 23 and the large diameter fiber 28 can be used as the light guide 33.

The light source 11 and the condenser lens 15 have a common optical axis L1. The light source 12 and the condenser lens 16 have a common optical axis L2. The light source 13 and the condenser lens 17 have a common optical axis L3. The light source 14 and the condenser lens 18 have a common optical axis L4. The light sources 11 to 14 and the condenser lenses 15 to 18 are placed such that optical axes L1 to L4 coincide with optical axes X1 to X4 of the small diameter fibers 20 to 23, respectively. Thereby, the light from the light sources 11 to 14 enters the small diameter fibers 20 to 23 via the condenser lenses 15 to 18, respectively.

Each of the small diameter fibers 20 to 23 and the large diameter fiber 28 is composed of a multimode optical fiber that transmits various modes of light. The outer diameter of a light incident surface of the large diameter fiber 28 is larger than the total outer diameter of the bundled small diameter fibers 20 to 23. As is well known, each of the small diameter fibers 20 to 23 and the large diameter fiber 28 is composed of a core, a clad surrounding the core, and when necessary, a protection layer (not shown) covering the clad. The outer diameter of the light incident surface of the large diameter fiber 28 is in a range from 2 mm to 40 mm. The total outer diameter of the bundled small diameter fibers 20 to 23 is in a range from 0.5 mm to 1.5 mm, and more preferably 1 mm. A core diameter of each of the small diameter fibers 20 to 23 is not less than 55 µm and not more than 65 µm, more preferably 60 µm. A clad diameter of each of the small diameter fibers 20 to 23 is not less than 75 µm and not more than 85 µm, and more preferably 80 µm.

The fiber connector 27 connects exit surfaces of the small diameter fibers 20 to 23 bundled together and a light incident surface of the large diameter fiber 28 via a protection medium (not shown). The exit light from the small diameter fibers 20 to 23 enters the large diameter fiber 28. A light amount distribution curve of the light in the large diameter fiber 28 has a substantially flat top, indicating that the amount of light (hereinafter, light amount) is substantially uniform and not less than a predetermined value across the diameter direction.

In the speckle reducer 30, the large diameter fiber 28 with several turns is vibrated to reduce speckle noise and to further increase the uniformity of the light amount distribution. Thereby, the light with the uniform light amount distribution is output from the light exit section 31. As a result, occurrence of the speckle noise is reduced.

Figure 2:
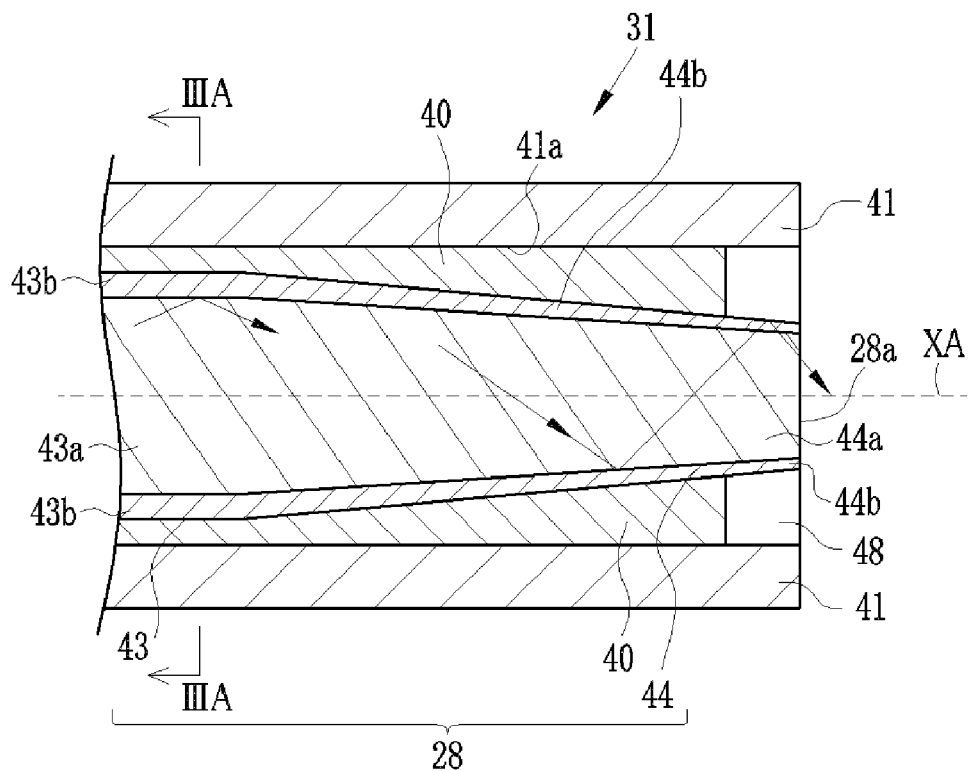
FIG. 2 is a cross-sectional view of a light exit section of the first embodiment of the present invention.

As shown in FIG. 2, in the light exit section 31, the large diameter fiber 28 is retained inside a retaining hole 41a of the tubular housing 41. The large diameter fiber 28 inside the tubular housing 41 is provided with a fiber body 43 and a tapered section 44. The fiber body 43 has a constant diameter in an optical axis direction XA. The tapered section 44 gradually tapers in the diameter direction toward a light exit surface 28a of the light exit section 31. The fiber body 43 is composed of a core 43a and a clad 43b. The clad 43b is provided on an outer circumferential surface of the core 43a, and has a constant thickness. The tapered section 44 is composed of a tapered core 44a and a tapered clad 44b provided on an outer circumferential surface of the tapered core 44a. The diameter of the tapered core 44a gradually decreases toward the light exit surface 28a. An outer circumferential surface of the tapered clad 44b is inclined to be tapered along the outer circumferential surface of the tapered core 44a toward the light exit surface 28a. The thickness of the tapered clad 44b decreases as it becomes closer to the light exit surface 28a. However, the tapered clad 44b may have a constant thickness. It is preferable that the tubular housing 41 is made from glass or the like.

In the fiber body 43, light propagates through the core 43a by total internal reflection at the interface between the core 43a and the clad 43b. On the other hand, in the tapered section 44, the light incident angle onto the tapered clad 44b becomes small. As a result, light not totally reflected at the interface between the core 43a and the clad 43b leaks to the tapered clad 44b. The outer circumferential surface of the tapered clad 44b contacts with a transparent adhesive member 40. The refractive index of the adhesive member 40 is lower than that of the tapered clad 44b. Accordingly, the light leaked to the tapered clad 44b is reflected off the interface between the tapered clad 44b and the adhesive member 40 by total internal reflection and is again transmitted through the tapered section 44.

Figure 3A:
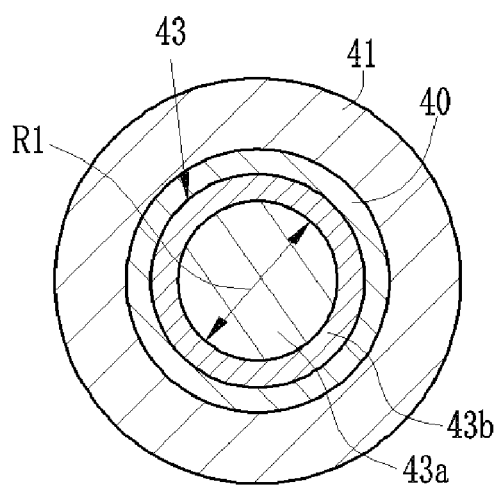
FIG. 3A is a cross-sectional view along a line IIIA-IIIA in FIG. 2.
Figure 3B:
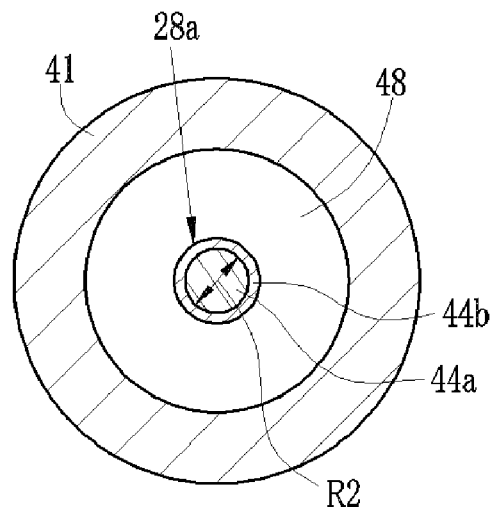
FIG. 3B is an end view of an exit surface containing a light exit surface of the light exit section.

As shown in FIG. 3A, a core outer diameter R1 of the fiber body 43 is not less than 225 µm and not more than 235 µm, and more preferably 230 µm. As shown in FIG. 3B, a core outer diameter R2 of the tapered section 44 at the light exit surface 28a is not less than 85 µm and not more than 100 µm, and more preferably 93 µm. A taper rate (tip-to-base diameter ratio of core outer diameter R2/core outer diameter R1) of the tapered section 44 is not less than 0.36 and not more than 0.44. It is preferable that a clad diameter of the large diameter fiber 28 is not less than 105 µm and not more than 255 µm.

The adhesive member 40 is composed of an optically transmissive adhesive, and hardened or cured with UV rays. As shown in FIG. 2, the adhesive member 40 attaches the large diameter fiber 28 in the retaining hole 41a such that the entire outer circumferential surface of the tapered clad 44b is exposed to air to a predetermined distance or depth from the light exit surface 28a. A refractive index of the adhesive member 40 is lower than those of the clad 43b and the tapered clad 44b of the large diameter fiber 28. Specifically, the refractive index (or indices) of the clad 43b and the tapered clad 44b is not less than 1.43 and not more than 1.44. It is preferable that the refractive index of the adhesive member 40 is not less than 1.40 and not more than 1.41.

A light passing space 48 is a ring-like space or end opening defined between an inner circumferential surface (inner surface) of the tubular housing 41 and an outer circumferential surface (hereinafter referred to as exposed area) of the tapered clad 44b which is exposed to a predetermined depth from the light exit surface 28a. The exposed area of the tapered clad 44b directly contacts with air in the light passing space 48. Accordingly, a critical angle for the total internal reflection at the interface between the tapered clad 44b and the light passing space 48 is larger than a critical angle at the interface between the tapered clad 44b and the adhesive member 40.

In the present invention, the divergence angle and the NA of the exit light are not restricted by the refractive indices of the core 43a, the tapered core 44a, the clad 43b, the tapered clad 44b, and the adhesive member 40. Instead, the divergence angle and the NA of the exit light can be adjusted to desired values by changing a taper rate of the tapered section 44 and a depth of the light passing space 48 in the optical axis direction XA, that is, the length of the exposed tapered clad 44b in the optical axis direction XA. It is possible to achieve the NA of at least 0.35 depending on the settings of the refractive indices of the core 43a, the tapered core 44a, the clad 43b and the tapered clad 44b.

Hereinafter, the increases in the divergence angle and the NA are described by comparing their numerical values in a case where neither the light passing space 48 nor the tapered section 44 is provided, in a case where only the tapered section 44 is provided, and in a case where both the light passing space 48 and the tapered section 44 are provided. In the case where neither the light passing space 48 nor the tapered section 44 is provided, the "NA1", that is, the maximum NA of a multimode optical fiber is calculated using the following mathematical expression (1) based on a refractive index Na of a core and a refractive index Nb of a clad.

$$NA1 = \sqrt{(Na^2 - Nb^2)} \quad (1)$$

For example, in a case where the refractive index Na of the core is 1.452 and the refractive index Nb of the clad is 1.436, the "NA1" is 0.22 and the maximum divergence angle is 24.2 degrees. Here, the core diameter of the fiber body 43 of the large diameter fiber 28 is 230 μm and the clad diameter thereof is 250 μm. In this case, the multimode optical fiber provided with neither the tapered section 44 (namely, the taper rate is 1.0) nor the light passing space 48 has a divergence angle of 16.0 degrees and the NA of 0.14.

On the other hand, in the case where only the tapered section 44 is provided, the "NA2", that is, the maximum NA of a multimode optical fiber is calculated using the following mathematical expression (2) based on a refractive index Na of the core and a refractive index Nc of the adhesive member.

$$NA2 = \sqrt{(Na^2 - Nc^2)} \quad (2)$$

For example, in a case where the refractive index Na of the core is 1.452, as with the above, and the refractive index Nc of the adhesive member is 1.407, the "NA2" is 0.36 and the maximum divergence angle is 42.2 degrees. This divergence angle is obtained where all light in the tapered section 44 is leaked from the tapered core 44a to the tapered clad 44b. In a case where the fiber body 43 having the core diameter of 230 μm and the clad diameter of 250 μm is provided with the tapered section 44 having a taper rate of 0.372 and the core diameter of 93 μm at the light exit surface 28a, the divergence angle is 37.6 degrees and the NA is 0.32. Thus, the divergence angle and the NA can be increased only by providing the tapered section 44.

The present invention is applied to the fiber body 43 having the core diameter of 230 μm and the clad diameter of 250 μm. In a case both the light passing space 48 and the tapered section 44 (the taper rate is 0.372 and the core diameter is 93 μm at the light exit surface 28a) are provided, the divergence angle becomes 47.0 degrees and the NA becomes 0.40. Thus, with the light passing space 48 in addition to the tapered section 44, the divergence angle and the NA are further increased to values larger than those in the case where only the tapered section 44 is provided.

The light passing space 48 is formed as follows. First, the large diameter fiber 28 is inserted into the retaining hole 41a of the tubular housing 41. The adhesive member 40 is provided between the outer circumferential surface of the large diameter fiber 28 and the inner circumferential surface of the tubular housing 41 such that the edges of the light exit surface 28a and the tubular housing 41 are level with each other. The adhesive member 40 is composed of a UV hardening or UV curable adhesive. The adhesive member 40 is irradiated with UV rays and hardened or cured. Thus, the large diameter fiber 28 is attached in the retaining hole 41a. Thereafter, laser having a wavelength in the UV range to be absorbed by the adhesive member 40 is irradiated to the entire end surface of the adhesive member 40 from the light exit surface 28a side, and thereby the adhesive member 40 is removed to a constant depth from the light exit surface 28a, which is called ablation. As a result, the entire outer circumferential surface of the tapered clad 44b is exposed to air to the constant depth from the light exit surface 28a. The light passing space 48 of a substantially annular cylindrical shape or ring-shape is formed between the exposed outer circumferential surface of the tapered clad 44b and the inner circumferential surface (inner surface) of the tubular housing 41.

It is preferable to use a single laser beam in which four laser beams each having the wavelength of 405 nm and output of 300 mW are multiplexed (total output is 1.2 W). It is preferable that the time required for the removal of the adhesive member 40 is approximately 5 minutes. Alternatively, laser with low power, for example, around 100 mW may be irradiated to the adhesive member 40 for a long time to alter the properties of the adhesive member 40. In this case, after the laser irradiation, the altered adhesive member 40 can be removed with a solvent such as acetone. Processing such as the removal of the adhesive is not normally performed after the edge polishing, because an edge, in this case, the light exit section of an optical connector is extremely fragile. In this embodiment, however, a non-contact processing method using laser irradiation is adopted. This processing method does not damage the edge even if the processing is performed after the edge polishing.

Figure 4:
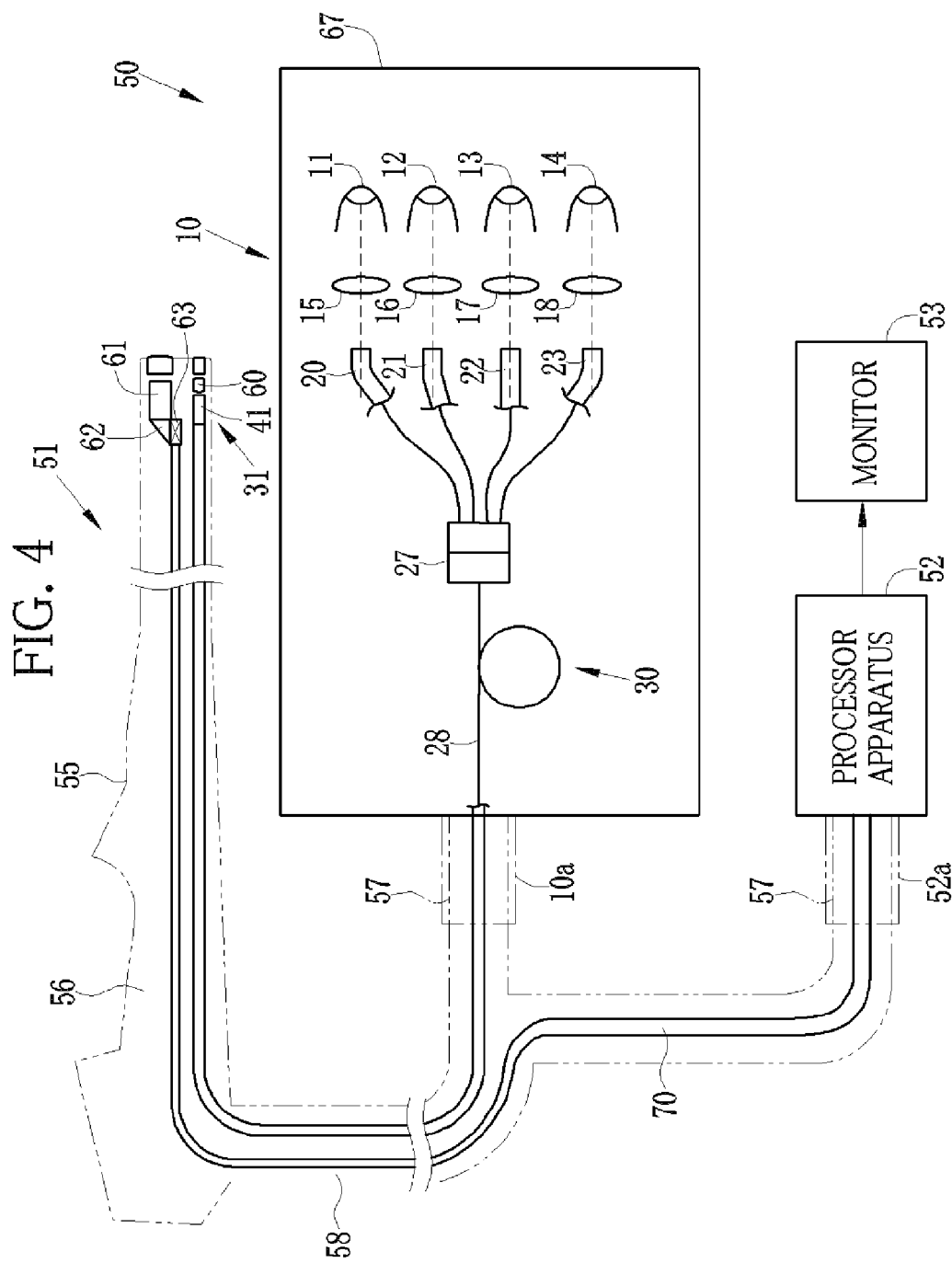
FIG. 4 is a schematic view of an endoscope system of the present invention.

As shown in FIG. 4, an endoscope system 50 uses the light source apparatus 10 as an apparatus for generating illumination light for illuminating a body cavity of a patient. An image of the body cavity illuminated with the illumination light is taken with an endoscope 51. A processor apparatus 52 or image processing apparatus performs various processing to the obtained image. Thereafter, the image is displayed on a monitor 53.

The endoscope 51 is provided with a flexible insert section 55 to be inserted in a body cavity of a patient, a handling section 56 provided at a base portion of the insert section 55 and used for operating the endoscope 51 with a hand, and a universal cord 58 for connecting universal connectors 57 and the handling section 56. The universal connectors 57 are attached to a socket 10*a* of the light source apparatus 10 and a socket 52*a* of the processor apparatus 52, respectively. In a distal end of the insert section 55 are provided an illumination optical system 60, an objective optical system 61, a prism 62 and an image sensor 63.

In a casing 67 are provided the light sources 11 to 14, the condenser lenses 15 to 18, the small diameter fibers 20 to 23, the fiber connector 27, and the speckle reducer 30 of the light source apparatus 10. An end portion of the large diameter fiber 28 is located inside the casing 67, and extends through the universal cord 58 and the insert section 55.

The light from the light sources 11 to 14 enters the small diameter fibers 20 to 23 via the condenser lenses 15 to 18, respectively. The light from the small diameter fibers 20 to 23 is output to the large diameter fiber 28 via the fiber connector 27. The light amount distribution of the light inside the large diameter fiber 28 is substantially uniform in the diameter direction with the light amount not less than the predetermined value. Uniformity of the light amount distribution of the light inside the large diameter fiber 28 is further increased in the speckle reducer 30, and then the light is transmitted to the light exit section 31.

The light from the light exit section 31 is further diffused in the illumination optical system 60 and then output to illuminate the body cavity. Since the divergence angle of the light output from the light exit section 31 is sufficiently increased with the use of the tapered section 44 and the light passing space 48, a wide illumination range is obtained without putting a burden on the illumination optical system 60. As a result, a substantially entire imaging area of the image sensor 63 is illuminated even if an object of interest is located at a close range, which facilitates finding a lesion from an image taken with the endoscope.

The image light reflected off the body cavity forms an image on an imaging surface of the image sensor 63 via the objective optical system 61 and the prism 62. Thereby, image signals of the image of the body cavity are obtained. The image signals are transmitted to the processor apparatus 52 through a signal line 70 in the insert section 55 and the universal cord 58. The processor apparatus 52 performs various processing to the image signals. The monitor 53 displays the image of the body cavity based on the processed image signals.

The light source apparatus of the second embodiment of the present invention has a similar configuration to the light source apparatus 10 of the first embodiment shown in FIG. 1 except for the light passing space provided in the light exit section. Therefore, descriptions other than those for the light passing space are omitted.

Figure 5:
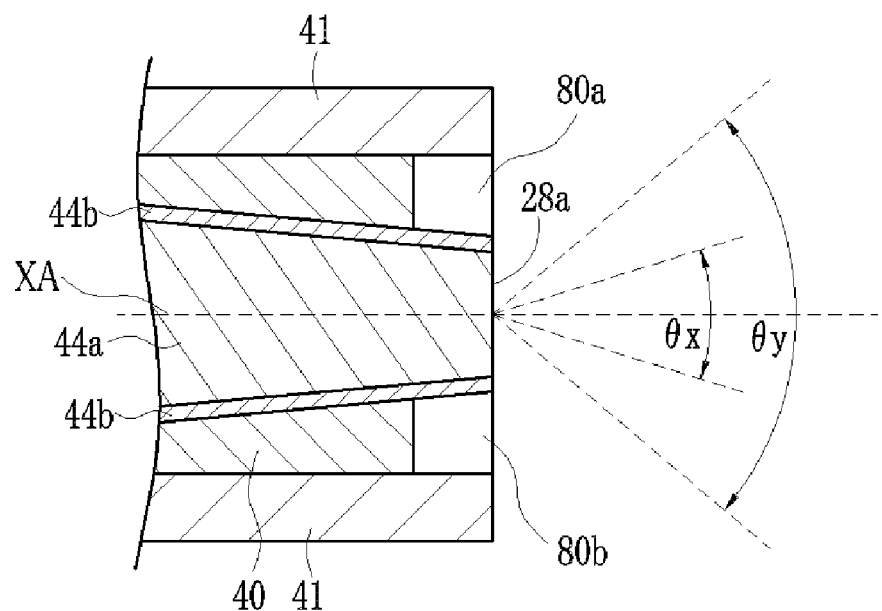
FIG. 5 is a cross-sectional view of a part of a light exit section of the second embodiment of the present invention.
Figure 6:
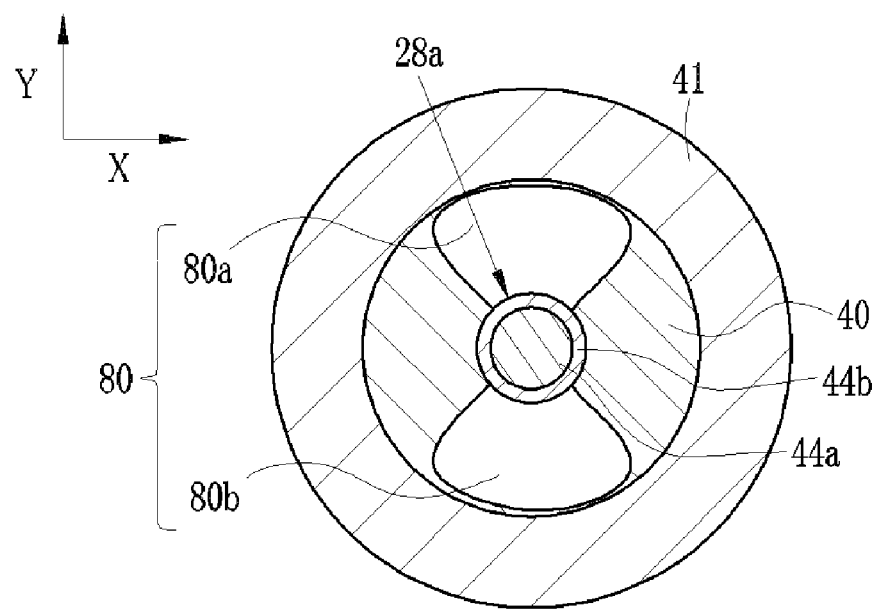
FIG. 6 is an end view of an exit surface of the light exit section of the second embodiment of the present invention.

The light passing space 48 of the first embodiment exposes the entire outer circumferential surface of the tapered clad 44*b* to air to a predetermined depth or distance from the light exit surface 28*a*, whereas a light passing space 80 or end opening of the second embodiment is formed so as to partly expose the outer circumferential surface of the tapered clad 44*b* to air as shown in FIGS. 5 and 6. The light passing space 80 is composed of a first space 80*a* and a second space 80*b* when the light exit surface 28*a* of the large diameter fiber 28 is viewed in a two-dimensional plane of X and Y-axes. The first space 80*a* is provided in a location opposite to the second space 80*b* relative to the tapered core 44*a* and the tapered clad 44*b*. For example, the first space 80*a* is provided above the tapered clad 44*b* (and the tapered core 44*a*) in the Y-axis direction. The second space 80*b* is provided below the tapered clad 44*b* (and the tapered core 44*a*) in the Y-axis direction. The first and second spaces 80*a* and 80*b* are in a tubular shape. The positions of the first and second spaces 80*a* and 80*b* are not limited to the above. The first and second spaces 80*a* and 80*b* may be provided on the right and left of the tapered clad 44*b* (and the tapered core 44*a*) in the X-axis direction. Methods for forming the first and second spaces 80*a* and 80*b* are the same as those described in the first embodiment except that the adhesive member 40 is partly removed, and the descriptions thereof are omitted.

As described above, with the use of the first and second spaces 80*a* and 80*b*, an area to be illuminated by the exit light containing light released from the first and second spaces 80*a* and 80*b* becomes larger in the Y-axis direction than in the X-axis direction. Therefore, as shown in FIG. 5, a divergence angle $\theta y$ in the Y-axis direction becomes larger than a divergence angle $\theta x$ in the X-axis direction. As a result, a radiation pattern of the exit light from the light exit section 31 becomes elliptical in shape. Changing depths of the first and second spaces 80*a* and 80*b* in the optical axis direction, the sizes of the first and second spaces 80*a* and 80*b* in the Y-axis direction, and the shapes of openings of the first and second spaces 80*a* and 80*b* through the exit surface of the light exit section 31 changes the divergence angle $\theta y$. Thereby, ellipticity or flattening ratio of the ellipsoidal radiation pattern can be adjusted.

Various changes and modifications are possible in the present invention and may be understood to be within the present invention.

What is claimed is:

1. A light guide for transmitting light and outputting said light from a light exit surface comprising:
   a tubular housing;
   a multimode optical fiber inserted through said housing, said multimode optical fiber having a core and a clad covering an outer circumferential surface of said core, said core having a tapered core whose diameter decreases toward said light exit surface, said clad having a tapered clad whose outer circumferential surface is inclined to be tapered along an outer circumferential surface of said tapered core toward said light exit surface, and
   a transparent adhesive member provided between said housing and an outer circumferential surface of said clad, said adhesive member retaining said multimode optical fiber in said housing, said adhesive member having a lower refractive index than said clad, said adhesive member having a light passing space hollowed out to a predetermined depth from said light exit surface so as to expose at least a part of said outer circumferential surface of said tapered clad to air.

2. The light guide of claim 1, wherein said light passing space is a ring-like space formed between an inner surface of said housing and said outer circumferential surface of said tapered clad entirely exposed to said air to said predetermined depth.

3. The light guide of claim 1, wherein said light passing space is composed of a first space and a second space, and each of said first and second spaces has a tubular shape and is formed between said partly exposed outer circumferential surface of said tapered clad and an inner surface of said housing, and said first space is provided in a location opposite to said second space relative to said tapered core and said tapered clad.

4. The light guide of claim 3, wherein a radiation pattern of said light from said light exit surface is elliptical in shape.

5. The light guide of claim 1, wherein a numerical aperture (NA) of said light from said light exit surface is at least 0.35.

6. A method of forming a light passing space of a light guide, comprising steps of:

inserting a multimode optical fiber into a housing, said multimode optical fiber having a core and a clad covering an outer circumferential surface of said core, said core having a tapered core whose diameter decreases toward a light exit surface, said clad having a tapered clad whose outer circumferential surface is inclined to be tapered along an outer circumferential surface of said tapered core toward said light exit surface;

attaching said multimode optical fiber in said housing by providing said adhesive member containing a UV hardening adhesive and by hardening said adhesive member by UV irradiation, and said adhesive member is provided between said outer circumferential surface of said clad and an inner surface of said housing in a state that said light exit surface of said multimode optical fiber and an end surface of said housing are made level with each other; and removing said adhesive member by irradiating laser in a UV wavelength range to be absorbed by said adhesive member onto said adhesive member such that at least a part of said outer circumferential surface of said tapered clad is exposed to said air to said predetermined depth from said light exit surface.

7. A light source apparatus comprising:

a light source;

a tubular housing;

a multimode optical fiber for transmitting light from said light source and inserted through said housing, said multimode optical fiber having a core and a clad covering an outer circumferential surface of said core, said core having a tapered core whose diameter decreases toward a light exit surface, said clad having a tapered clad whose outer circumferential surface is inclined to be tapered along an outer circumferential surface of said tapered core toward said light exit surface; and a transparent adhesive member provided between said housing and an outer circumferential surface of said clad, said adhesive member retaining said multimode optical fiber in said housing, said adhesive member having a lower refractive index than said clad, said adhesive member having a light passing space hollowed out to a predetermined depth from said light exit surface so as to expose at least a part of said outer circumferential surface of said tapered clad to air.

8. An endoscope system comprising:

A. a light source apparatus including:

a light source;

a tubular housing;

a multimode optical fiber for transmitting light from said light source and inserted through said housing, said multimode optical fiber having a core and a clad covering an outer circumferential surface of said core, said core having a tapered core whose diameter decreases toward a light exit surface, said clad having a tapered clad whose outer circumferential surface is inclined to be tapered along an outer circumferential surface of said tapered core toward said light exit surface; and a transparent adhesive member provided between said housing and an outer circumferential surface of said clad, said adhesive member retaining said multimode optical fiber in said housing, said adhesive member having a lower refractive index than said clad, said adhesive member having a light passing space hollowed out to a predetermined depth from said light exit surface so as to expose at least a part of said outer circumferential surface of said tapered clad to air;

B. an endoscope having an image sensor, said image sensor taking an image of a body cavity illuminated with said light from said light exit surface; and C. an image processing apparatus connected to said endoscope, said processing apparatus processing a signal from said image sensor and forming an image.

* * * * *